(12) United States Patent
Click et al.

(10) Patent No.: US 8,372,082 B2
(45) Date of Patent: Feb. 12, 2013

(54) SURGICAL APPARATUS WITH FORCE LIMITING CLUTCH

(75) Inventors: Bryan A. Click, Fremont, CA (US); Brian W. Donovan, San Jose, CA (US)

(73) Assignee: Kyphon SARL, Neuchatel (CH)

( * ) Notice: Subject to any disclaimer, the term of this patent is extended or adjusted under 35 U.S.C. 154(b) by 660 days.

(21) Appl. No.: 12/512,937

(22) Filed: Jul. 30, 2009

(65) Prior Publication Data

US 2011/0024145 A1 Feb. 3, 2011

(51) Int. Cl.
*A61B 17/58* (2006.01)

(52) U.S. Cl. ............................................. 606/92; 173/4

(58) Field of Classification Search .............. 606/92–95; 173/2–11, 176–183; 433/89, 90; 222/386, 222/386.5
See application file for complete search history.

(56) References Cited

U.S. PATENT DOCUMENTS

| | | | |
|---|---|---|---|
| 4,966,601 A | 10/1990 | Draenert | |
| 4,973,334 A | 11/1990 | Ziemann | |
| 5,137,181 A * | 8/1992 | Keller | 222/134 |
| 5,514,135 A | 5/1996 | Earle | |
| 5,954,728 A * | 9/1999 | Heller et al. | 606/92 |
| 6,086,594 A | 7/2000 | Brown | |
| 6,348,055 B1 | 2/2002 | Preissman | |
| 7,008,433 B2 | 3/2006 | Voellmicke et al. | |
| 7,112,205 B2 | 9/2006 | Carrison | |
| 2004/0122438 A1 | 6/2004 | Abrams | |
| 2005/0070915 A1 | 3/2005 | Mazzuca et al. | |
| 2005/0113843 A1 | 5/2005 | Arramon | |
| 2005/0180806 A1 | 8/2005 | Green et al. | |
| 2006/0052794 A1 | 3/2006 | McGill et al. | |
| 2006/0074433 A1 | 4/2006 | McGill et al. | |
| 2006/0264967 A1 | 11/2006 | Ferreyro et al. | |
| 2006/0266372 A1 | 11/2006 | Miller et al. | |
| 2007/0027230 A1 | 2/2007 | Beyar et al. | |
| 2008/0027456 A1 | 1/2008 | Truckai et al. | |
| 2008/0039856 A1 | 2/2008 | DiMauro et al. | |

* cited by examiner

*Primary Examiner* — Nicholas Woodall
*Assistant Examiner* — Melissa A Hall
(74) *Attorney, Agent, or Firm* — Sorell, Lenna and Schmidt LLP (57) ABSTRACT

A force-limiting clutch for a surgical instrument includes a drive element and a transmission element. An actuator is coupled to the drive element, and a drive shaft is coupled to the transmission element for providing an output force. If the force input from the actuator to the clutch reaches a predetermined threshold, the force-limiting clutch "slips" and does not transfer the actuator force to the drive shaft to prevent excessive force/pressure output. Normally, drive features on the drive element engage with transmission features on the transmission element to transfer forces from the actuator to the drive shaft. When a threshold force is reached, the drive features slip past the transmission features. This clutch "breakpoint" determines the maximum loading that the surgical instrument can provide at its output. In various embodiments, multiple transmission features can be arranged in a serial manner, such that the force-limiting clutch provides multiple breakpoints.

20 Claims, 10 Drawing Sheets

SURGICAL APPARATUS WITH FORCE LIMITING CLUTCH

FIELD OF THE INVENTION

The invention relates to a system and method for performing a surgical procedure, and in particular, to a system for preventing the generation of excessive loading forces in a surgical system.

BACKGROUND OF THE INVENTION

A minimally invasive procedure is a medical procedure that is performed through the skin or an anatomical opening. In contrast to an open procedure for the same purpose, a minimally invasive procedure will generally be less traumatic to the patient and result in a reduced recovery period.

However, there are numerous challenges that minimally invasive procedures present. For example, minimally invasive procedures are typically more time-consuming than their open procedure analogues due to the challenges of working within a constrained operative pathway. In addition, without direct visual feedback into the operative location, accurately selecting, sizing, placing, and/or applying minimally invasive surgical instruments and/or treatment materials/devices can be difficult.

For example, for many individuals in our aging world population, undiagnosed and/or untreatable bone strength losses have weakened these individuals' bones to a point that even normal daily activities pose a significant threat of fracture. In one common scenario, when the bones of the spine are sufficiently weakened, the compressive forces in the spine can cause fracture and/or deformation of the vertebral bodies. For sufficiently weakened bone, even normal daily activities like walking down steps or carrying groceries can cause a collapse of one or more spinal bones. A fracture of the vertebral body in this manner is typically referred to as a vertebral compression fracture. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Until recently, treatment options for vertebral compression fractures, as well as other serious fractures and/or losses in bone strength, were extremely limited—mainly pain management with strong oral or intravenous medications, reduced activity, bracing and/or radiation therapy, all with mediocre results. Because patients with these problems are typically older, and often suffer from various other significant health complications, many of these individuals are unable to tolerate invasive surgery. In addition, to curb further loss of bone strength, many patients are given hormones and/or vitamin/mineral supplements—again with mediocre results and often with significant side effects.

In an effort to more effectively and directly treat vertebral compression fractures, minimally invasive techniques such as vertebroplasty and, subsequently, kyphoplasty, have been developed. Vertebroplasty involves the injection of a flowable reinforcing material, usually polymethylmethacrylate (PMMA—commonly known as bone cement), into a fractured, weakened, or diseased vertebral body. Shortly after injection, the liquid filling material hardens or polymerizes, desirably supporting the vertebral body internally, alleviating pain and preventing further collapse of the injected vertebral body.

Because the liquid bone cement naturally follows the path of least resistance within bone, and because the small-diameter needles used to deliver bone cement in vertebroplasty procedure require either high delivery pressures and/or less viscous bone cements, ensuring that the bone cement remains within the already compromised vertebral body is a significant concern in vertebroplasty procedures. Kyphoplasty addresses this issue by first creating a cavity within the vertebral body (e.g., with an inflatable balloon) and then filling that cavity with bone filler material. The cavity provides a natural containment region that minimizes the risk of bone filler material escape from the vertebral body. An additional benefit of kyphoplasty is that the creation of the cavity can also restore the original height of the vertebral body, further enhancing the benefit of the procedure.

In many cases, enhancements to existing minimally invasive surgical procedures, or new applications for minimally invasive surgical procedures, necessitate the use of higher pressures to perform those procedures (e.g., the use of more viscous bone filler materials in vertebroplasty or kyphoplasty to reduce extravasation risks, or the use of smaller cement delivery needles/nozzles to enhance placement flexibility and/or reduce patient trauma). However, as higher-pressure tools are developed, it becomes more critical that overpressure conditions do not develop that could result in adverse results for patients.

Accordingly, it is desirable to provide surgical tools and techniques that limit forces and/or pressures generated by or within surgical systems.

SUMMARY OF THE INVENTION

By incorporating a force-limiting mechanism into the actuator of a surgical system, problematic overload conditions during use of the surgical system can be avoided.

In one embodiment, a surgical instrument includes a force-limiting clutch that includes a drive element and a transmission element. The surgical instrument further includes an actuator coupled to the drive element, and a drive shaft coupled to the transmission element, the drive shaft providing an output force to the effector of the surgical instrument (e.g., a material delivery system or a bone manipulation system). If the force input from the actuator to the clutch reaches a predetermined threshold, the force-limiting clutch "slips" and does not transfer the actuator force to the drive shaft. In this manner, the force-limiting clutch prevents excessive force or pressure generation at the output of the surgical instrument, thereby enhancing safety and reliability.

In one embodiment, the drive element includes one or more drive features, and the transmission element includes one or more transmission features. During normal operation, the drive features engage with the transmission features to allow the drive element to transfer forces from the actuator to the drive shaft. However, when the force input from the actuator reaches a threshold force, the drive features slip past the transmission features. This clutch "breakpoint" determines the maximum loading that the surgical instrument can apply at its output.

In various embodiments, multiple transmission features can be arranged in a serial manner, such that the force-limiting clutch provides multiple breakpoints. Each breakpoint can be tripped by the same force, or different breakpoints can respond to different input forces. In one embodiment, a series of breakpoints for the force-limiting clutch can be configured such that each successive breakpoint trips at a higher force.

In other embodiments, the transmission element includes one or more support structures on which the transmission features are located. The support structures are flexibly biased toward the drive element (e.g., cantilevered, spring-loaded, or otherwise resiliently loaded), such that the support structures move outward and then back into place as the drive features slide past the transmission features when a clutch breakpoint trips. In one embodiment, the support structures are configured to snap back into place and create an audible and/or tactile indication a clutch breakpoint has tripped.

After one or more clutch breakpoints have tripped, the force-limiting clutch can be reset by simply putting the actuator in a direction opposite to the direction of actuation. In various embodiments, the transmission features and/or the drive features are configured such that force required to slip the drive features past the transmission features in the actuation direction (i.e., the force required to trip a clutch breakpoint) is much greater than the force required to slip the drive features past the transmission features in the reverse direction (i.e., the force required to reset the clutch). In one embodiment, the drive and transmission features can be protrusions or teeth on the surfaces of the drive and transmission elements, respectively. The reduced reset force can then be enabled by giving the drive and/or transmission features steeply angled leading surfaces (i.e., the contact surfaces for normal operation of the clutch) and gently angled trailing surfaces (i.e., the surfaces that engage during a clutch reset operation).

As will be realized by those of skilled in the art, many different embodiments of surgical instruments incorporating a force-limiting clutch according to the present invention are possible. Additional uses, advantages, and features of the invention are set forth in the illustrative embodiments discussed in the detailed description herein and will become more apparent to those skilled in the art upon examination of the following.

DETAILED DESCRIPTION

By incorporating a multi-stage force transmission mechanism into a surgical instrument, overload signaling and prevention can be provided in a compact construction to enhance the usability and safety of the surgical instrument.

Figure 1:
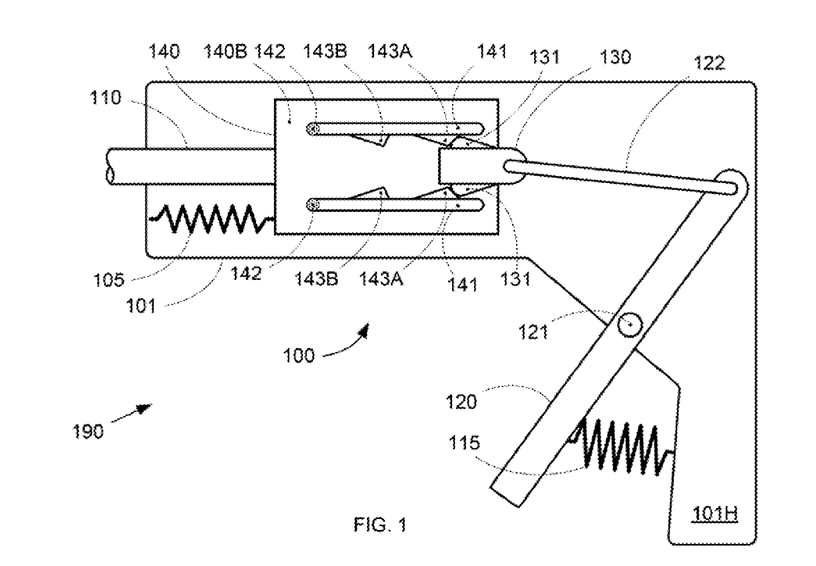
FIGS. 1-2 are diagrams depicting the normal operation of a surgical instrument incorporating a force-limiting clutch.

FIG. 1 shows a diagram of a surgical instrument 190 that includes a force-limiting clutch 100. Surgical instrument 190 further includes a housing 101, an actuator 120 coupled to housing 101 that allows a user to input a force to surgical instrument 190, and a drive shaft 110 that transmits the force to the output of surgical instrument 190. Drive shaft 110 can be any element for transferring the force from force-limiting clutch, such as a solid bar, rod, or plate, the core of a push-pull cable, or a cable for a pulley system, among other options.

Force-limiting clutch 100 includes a drive element 130 coupled to actuator 120, and a transmission element 140 coupled to drive shaft 110. For exemplary purposes, actuator 120 is coupled to drive element 130 by a drive linkage 122. However, in various other embodiments, actuator 120 could be coupled to drive element 130 by any mechanism (e.g., pulleys, gears, threaded elements, or even directly). Likewise, while drive shaft 110 is coupled directly to transmission element 140 for exemplary purposes, in various other embodiments, drive element 110 could be coupled via any type of mechanism to transmission element 140.

Within force-limiting clutch 100, drive element 130 includes one or more drive features 131, while transmission element 140 includes one or more interfacing transmission features 143 formed on support elements 141. Support elements 141 are cantilevered off of the body (housing) 140B of transmission element 140 (e.g., at attachment regions 142), and can therefore move (flex) with respect to body 140B. As described in greater detail below, the engagement state of drive features 131 with transmission features 143 determines the actual force (or lack thereof) transferred from actuator 120 to drive shaft 110.

Note that while a single pair of drive features 131 and two pairs of transmission features 143 (i.e., features 143A and 143B) are depicted for exemplary purposes, in various other embodiments, force-limiting clutch 100 can include any number of drive and transmission features. For example, in one embodiment, drive element 130 could include only a single drive feature (e.g., a drive feature on only one side of drive element 130, or drive element 130 itself could be the drive feature). In another embodiment, drive element 130 could include a series of drive features that engage singly or multiply with transmission features on transmission element 140. Likewise, transmission element 140 can include any number and arrangement of transmission features 143.

Figure 2:
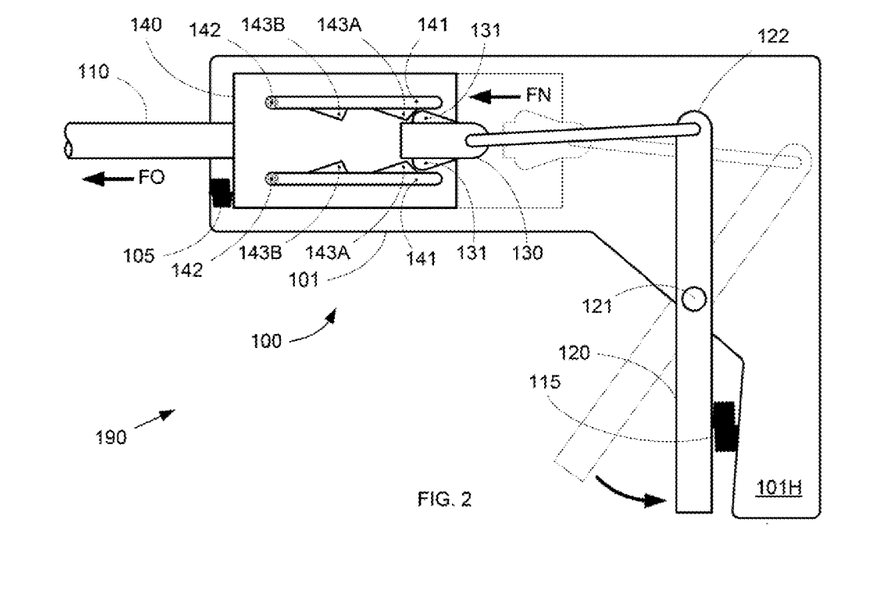

As shown in FIG. 2, during normal operation of surgical instrument 190 (i.e., the force FN applied by actuator 120 is less than a threshold force), force-limiting mechanism 100 acts like a direct connection between actuator 120 and drive shaft 110. Specifically, drive features 131 of drive element 130 abut transmission features 143A of transmission element 140, such that drive element 130 and transmission element 140 move as a single unit. Thus, during normal operation of surgical instrument 190, pulling actuator 120 towards a handle portion 101H of housing 101 moves drive shaft 110 forward directly, and an output force FO generated at drive shaft 110 is equal to the input force FN applied by actuator 122 to force-limiting clutch 100.

Releasing actuator 120 then allows surgical instrument 190 to reset, with actuator 120 and force-limiting clutch 100 moving back to their original positions (as shown in FIG. 1). This resetting operation is enabled by return mechanisms 115 and 105 for actuator 120 and force-limiting clutch, respectively. Return mechanism 115 is a resilient element (e.g., a spring or elastomeric element) coupled between actuator 120 and handle portion 101H of housing 101 that pushes the two apart. Return mechanism 105 is another resilient element that is coupled between housing 101 and force-limiting element 100 that pushes force-limiting element back to its original baseline position within housing 101. Note that while return mechanisms 115 and 105 are depicted as spring-type elements for exemplary purposes, in various other embodiments any type of resilient element(s) or mechanisms could be used.

In addition, the particular combination and placements of return mechanisms 105 and 115 are for exemplary purposes, and in various other embodiments, return mechanisms 105 and 115 can be anywhere that provides the desired (default) positioning effect. For example, in one embodiment, return mechanism 115 could be removed, with return mechanism 105 returning both force-limiting clutch 100 and actuator 120 (via clutch 100) back to their baseline positions.

Figure 2A:
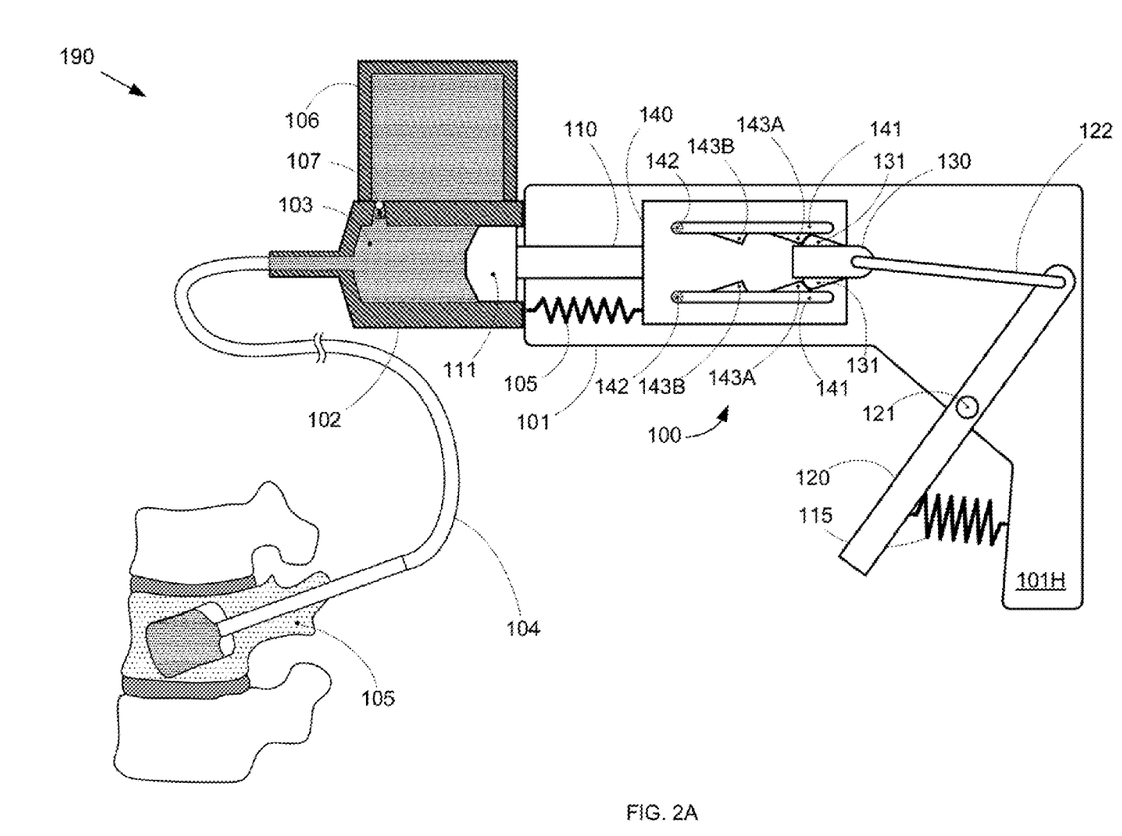
FIGS. 2A and 2B are diagrams of various alternative surgical instruments incorporating the force-limiting clutch of FIGS. 1-2.

Note that surgical instrument 190 can be any type of surgical system in which overload prevention would be beneficial. For example, surgical instrument 190 is depicted in FIG. 2A as a bone filler material delivery system for performing vertebroplasty or kyphoplasty. A plunger tip 111 at the end of shaft 110 drives bone filler material 103 (e.g., bone cement) from a barrel (chamber) 102 through a delivery path 104 (e.g., a flexible tube and delivery needle/nozzle) into a vertebral body 105. Retracting plunger tip 111 then refills barrel 102 from a reservoir 106 via a check valve 107. As more of bone filler material 103 is pumped into vertebral body 105, the delivery pressure increases. Overpressurization of the bone filler material 103 in vertebral body 105 can then be prevented by the action of force-limiting clutch 100 (as described in greater detail below), thereby minimizing extravasation risks.

Figure 2B:
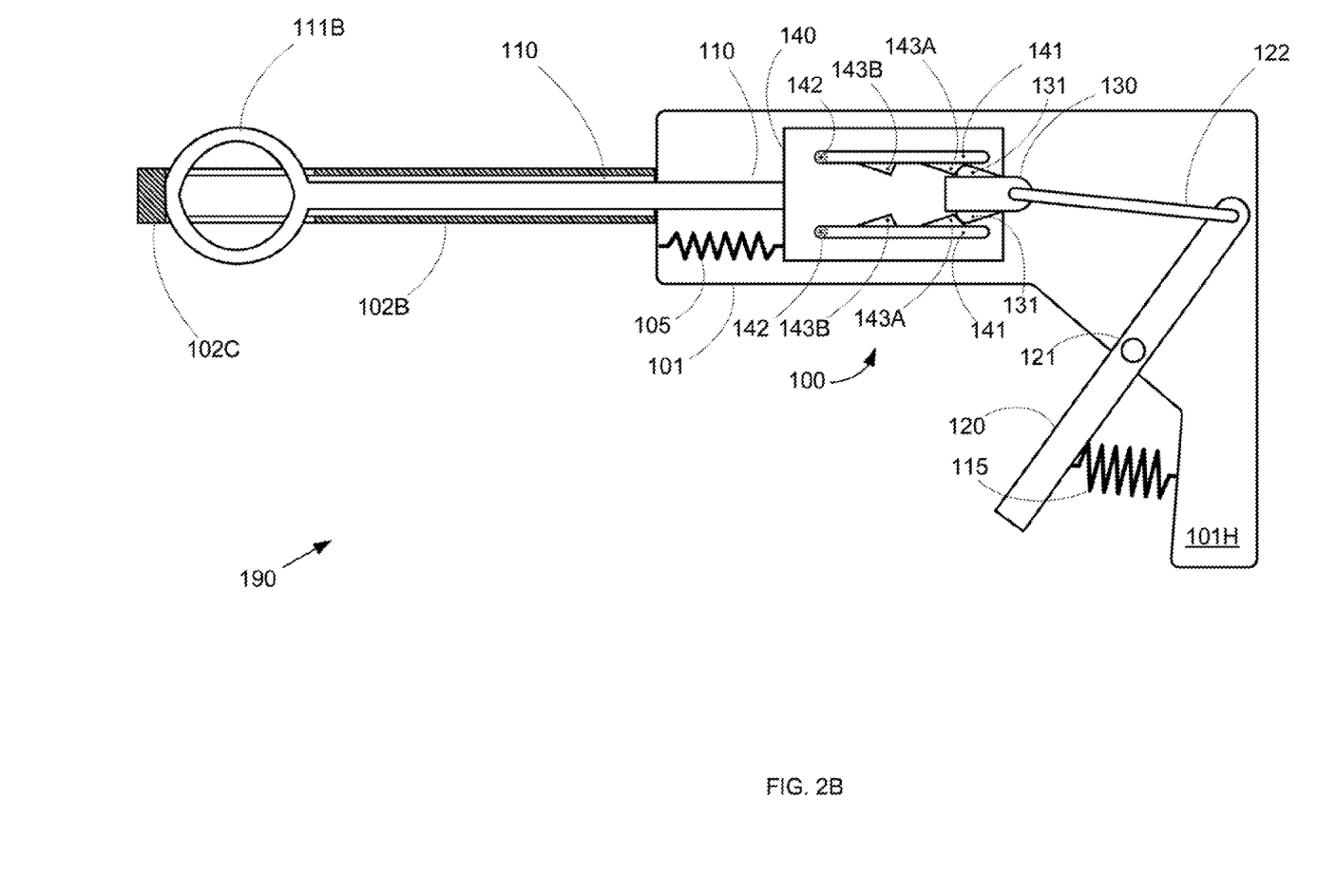

FIG. 2B shows an alternative embodiment of surgical instrument 190 in which shaft 110 includes an expandable element 111B that can be used for bone manipulation (e.g., cavity creation within cancellous bone or restoring vertebral endplate position after a fracture has occurred). As shaft 110 is advanced through a sheath 102B, expandable element 111B is compressed against a solid tip 102C of sheath 102B, and expands outwards in response. Here, force-limiting clutch 100 can prevent expandable element 111B from exerting excessive force on the bone to prevent, for example, endplate breach when attempting to restore vertebral body height after a compression fracture. Various other embodiments of surgical instruments incorporating force-limiting clutch 100 will be readily apparent.

Figure 2C:
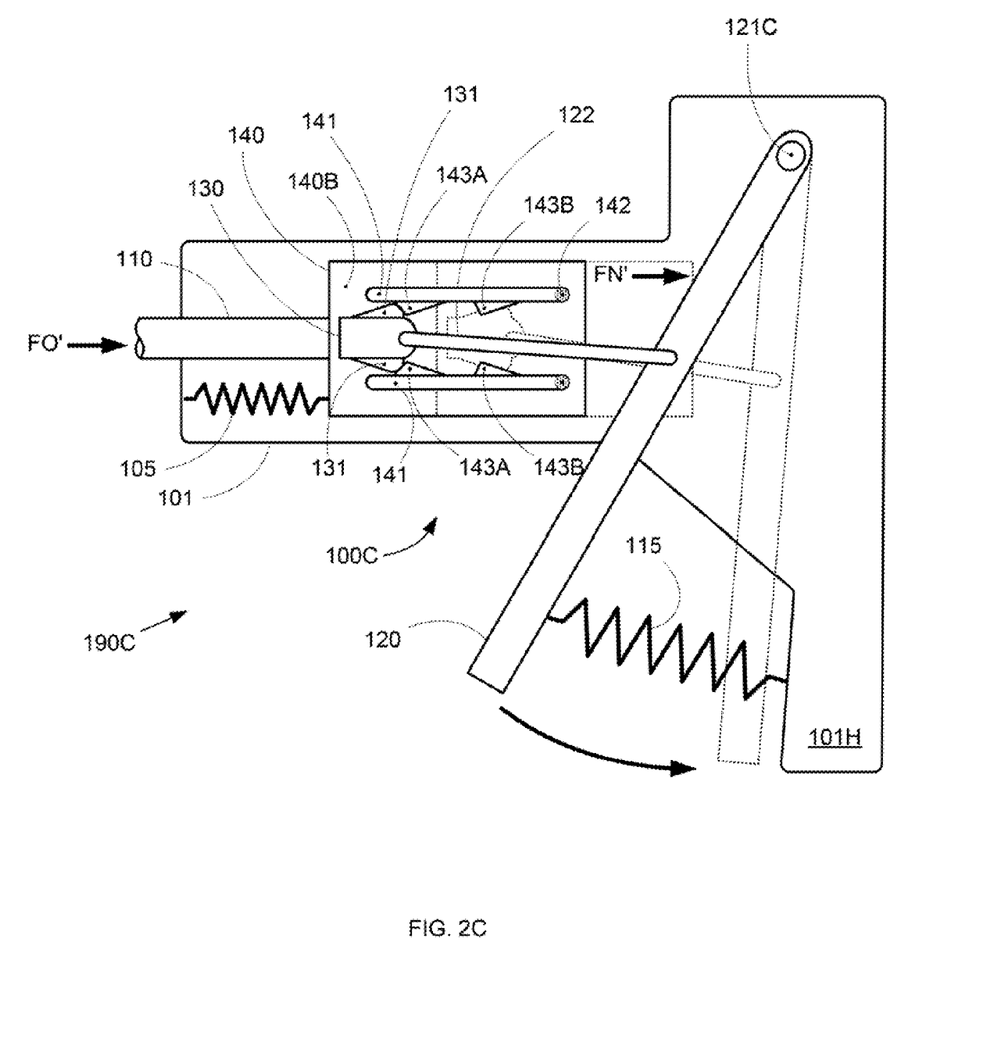

Note that although force-limiting clutch 100 is described as transmitting an advancement (pushing) force from actuator 120 to drive shaft 110 for exemplary purposes, in various other embodiments, force-limiting clutch 100 can be used to transmit a retraction (pulling) force from actuator 120 to drive shaft 110. FIG. 2C shows an embodiment of surgical instrument 190C that includes a force-limiting clutch 100C that operates substantially similarly to force-limiting clutch 100 in FIGS. 1-2, except in a reverse direction. Specifically, a pivot point 121C for actuator 120 of surgical instrument 190C is located such that pulling actuator 120 towards handle portion 101H applies a force FN' that pulls clutch 100C distally, thereby imparting a corresponding retraction force FO' at drive shaft 110. The force-limiting functionality of clutch 100C is then provided in substantially the same manner as that of clutch 100 shown in FIGS. 1-2, as described in greater detail below.

Figure 3:
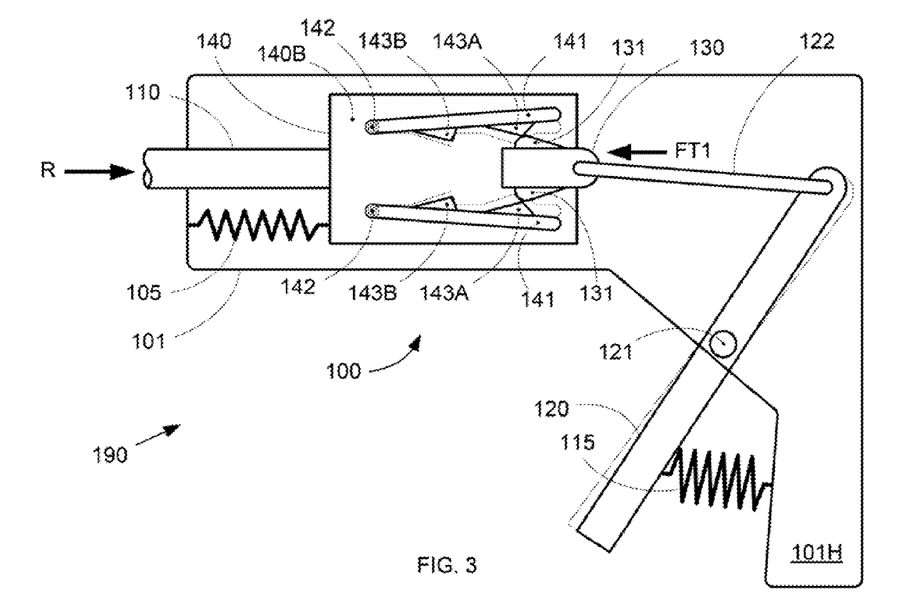
FIGS. 3-10 are diagrams of the force-limiting clutch of FIGS. 1-2 tripping multiple breakpoints and being reset.
Figure 4:
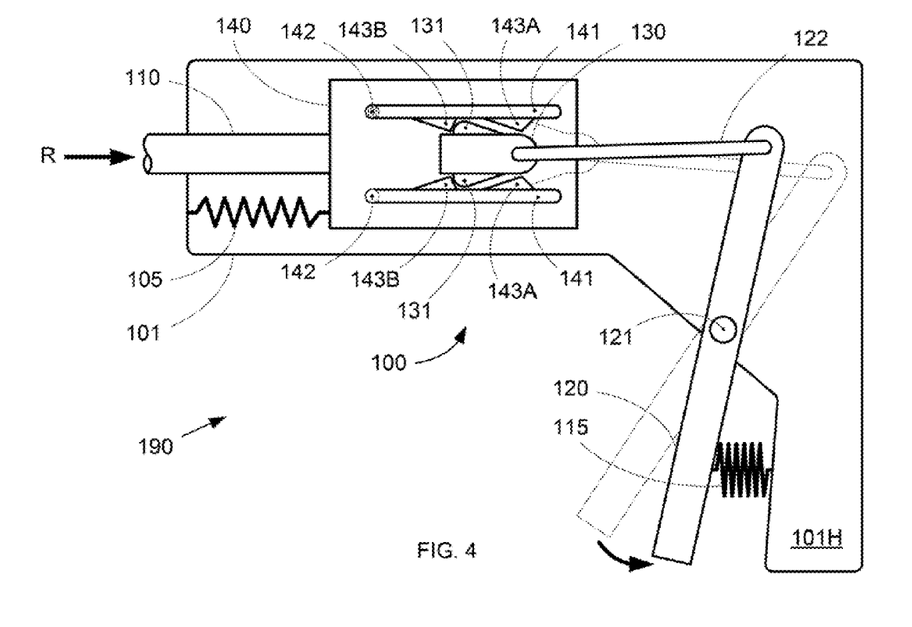

In any event, as drive shaft 110 encounters increasing resistance (e.g., due to pressure buildup in a cement delivery syringe or resistance encountered by an expandable bone cavity creation structure), the force being applied to force-limiting clutch 100 by actuator 120 increases as well. Once this applied force provided at drive shaft 110 reaches a threshold force FT1, force-limiting clutch 100 no longer behaves like a solid connection to actuator 120. As shown in FIG. 3, in response to threshold force TF at force-limiting clutch 100, drive element 130 begins to "slip" with respect to transmission element 140. Specifically, drive features 131 begin to wedge between transmission features 143A. The cantilevered support structures 141 on which transmission features 143A are located flex apart in response to this wedging action, ultimately allowing drive features 131 to pass to the opposite side of transmission features 143A, as shown in FIG. 4.

Note that the particular threshold force FT required to trip this first clutch breakpoint (i.e., the first point at which drive element 130 slips relative to transmission element 140) is determined by many factors, including the configuration of support elements 141 (e.g., the amount of cantilever, the rigidity of the elements, the relative angle of the elements, etc.) and the configuration of the drive features 131 and transmission features 143 (e.g., quantity, angle of incidence, surface roughness, materials, etc.), among others. Therefore, by properly sizing and configuring drive features 131 transmission features 143A, and support elements 141, force-limiting clutch 100 can be designed to have a first breakpoint at any desired threshold force.

The cantilevered support elements 141 that allow drive element 130 to slip past transmission features 143A will tend to spring back into place once drive features 131 have fully passed transmission features 143A. Therefore, in various embodiments, force-limiting clutch 100 can be configured such that this snap back of cantilevered support elements 141 creates an audible and/or tactile indication (e.g., transmission features 143A or support element 141 striking drive element 130) that the first clutch breakpoint has been tripped. The sound and/or feeling provided by this snap back can then provide an indication to the user of surgical instrument 190 that an overload condition has been reached.

Immediately after the first clutch breakpoint has been tripped, continued pressure on actuator 120 will cause drive features 131 of drive element 130 to be pressed against transmission features 143B of transmission element 140. If the force applied to drive element 130 by actuator 120 is less than a second threshold force FT2, force-limiting mechanism 100 will act like a direct connection between actuator 120 and drive shaft 110.

Figure 5:
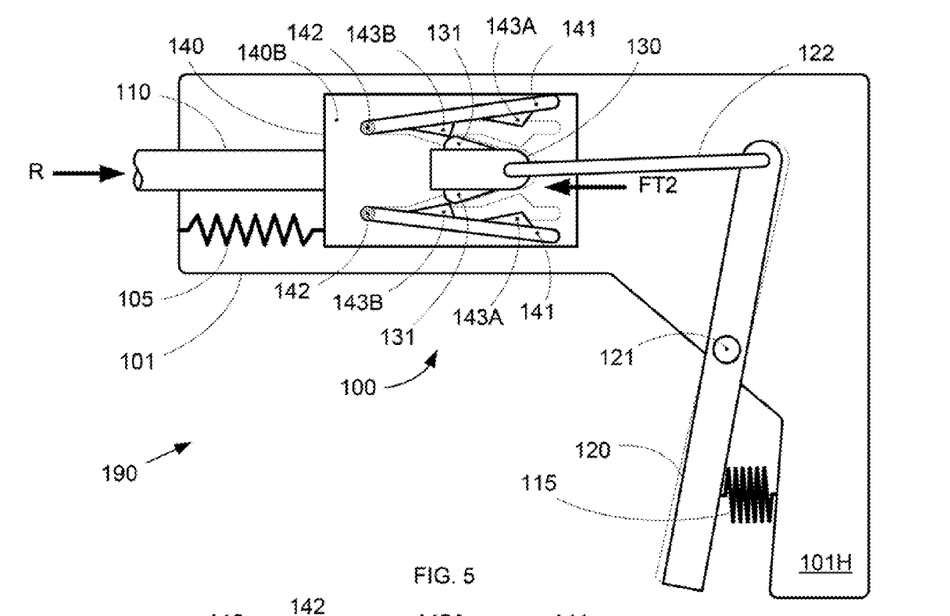
Figure 6:
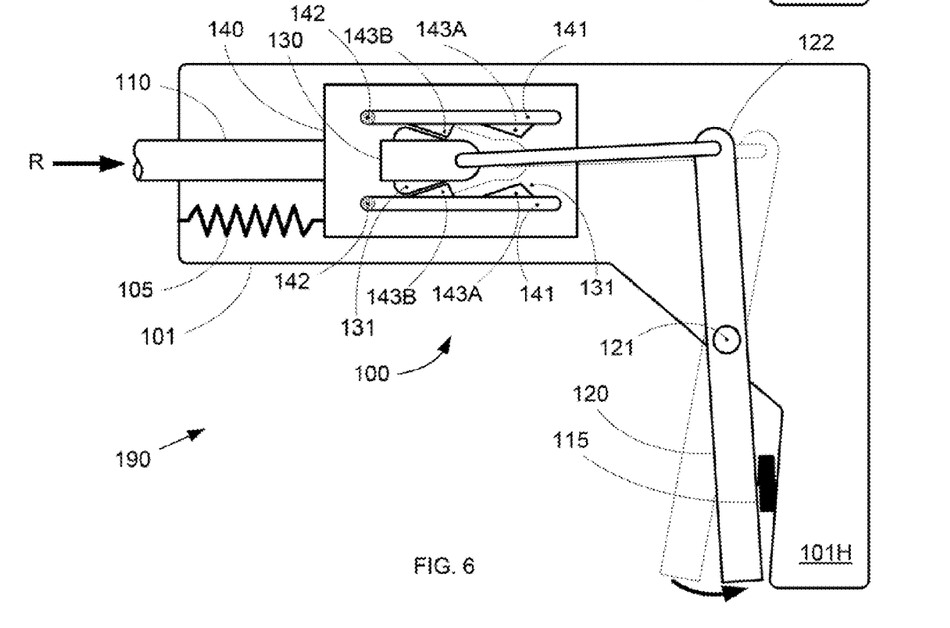

However, once the force applied to drive element 130 reaches the second threshold force FT2, drive element 130 will again slip with respect to transmission element 140. Specifically, drive features 131 begin to wedge between transmission features 143B, as shown in FIG. 5. Cantilevered support structures 141 on which transmission features 143B are located once again flex apart in response to this wedging action, ultimately allowing drive features 131 to pass to the opposite side of transmission features 143B, as shown in FIG. 6. Once again, drive element 130 and transmission element 140 can be configured such that when support elements 141 snap back in to place after drive features 131 have moved past transmission features 143B, an audible and/or tactile indication is generated.

Once this second clutch breakpoint has been tripped, force-limiting clutch 100 can no longer transfer any actuation force from actuator 120 to drive shaft 110, and force-limiting clutch 100 is essentially disabled. Therefore, by configuring force-limiting clutch 100 such that second threshold force FT2 is the maximum allowable force for the output of surgical instrument 190, overload situations for surgical instrument 190 can be prevented.

Note that in some embodiments, the threshold forces FT1 and FT2 required to trip the first and second clutch breakpoints, respectively, of force-limiting clutch 100 can be selected to be the same. Alternatively, in various other embodiments, threshold forces FT1 and FT2 can be different. For example, threshold force FT1 may be lower than threshold force FT2 to provide a "pre-limit" warning at the first clutch breakpoint that the loading is reaching the operating maximum, before clutch 100 is disabled at the second breakpoint.

Note further that while force-limiting clutch 100 is described as having two breakpoints for exemplary purposes, in various other embodiments, force-limiting clutch 100 can have any number of breakpoints. For example, clutch 100 could include only a single breakpoint (e.g., transmission element 140 could include only transmission features 143A, and not transmission features 143B) such that clutch 100 is disabled as soon as threshold force FT1 is reached. Alternatively, transmission element 140 could include multiple additional transmission features 143 (in addition to features 143A and 143B), such that force-limiting clutch 100 would continue to operate after an overload condition if subsequent loading from actuator 120 remained below the threshold force for the remaining breakpoints.

Figure 7:
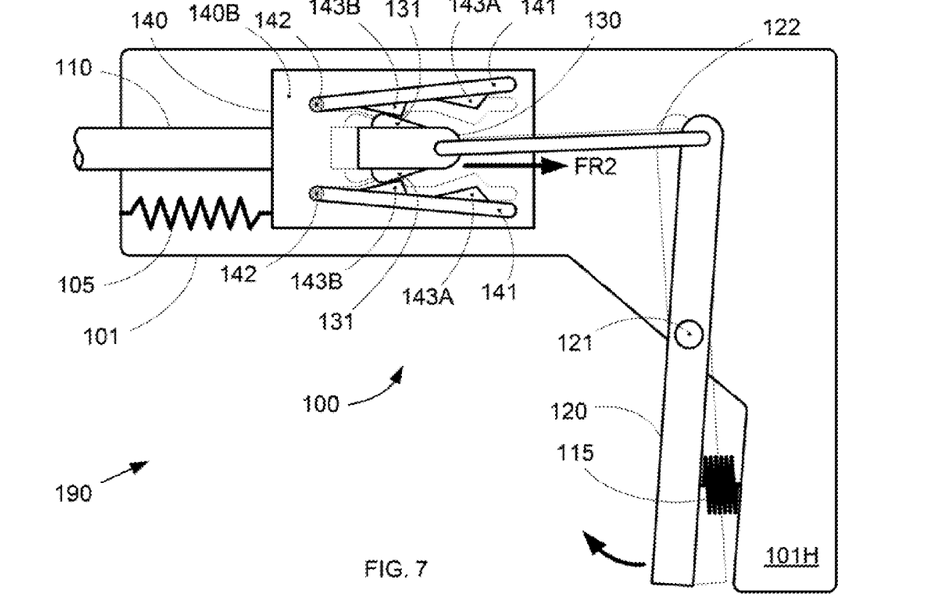
Figure 8:
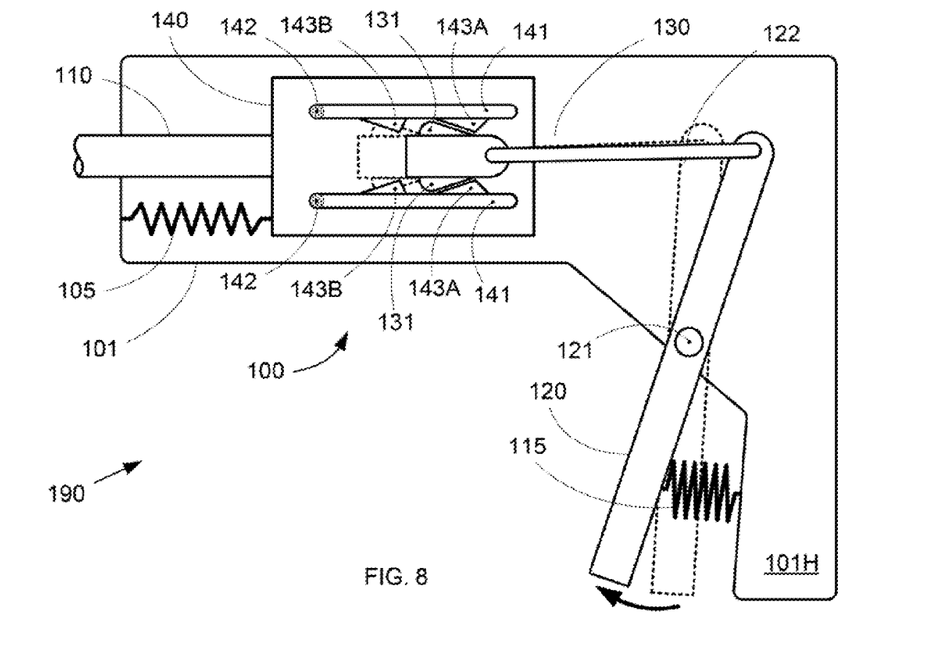

To reset force-limiting clutch 100 after one or more breakpoints have been tripped, actuator 120 can simply pulled in a direction opposite that of the actuation direction. In the exemplary embodiment, actuation is performed by pulling actuator 120 towards handle 101H. Therefore, to begin the reset process actuator 120 can be pulled away from handle 101H, as shown in FIG. 7. Once the force applied to drive element 130 reaches a first reset force FR1, drive features 131 begin to wedge between transmission features 143B. Cantilevered support structures 141 flex apart in response to this wedging action, ultimately allowing drive features 131 to pass to the opposite side of transmission features 143B as shown in FIG. 8, thereby resetting the second break point of clutch 100.

Figure 9:
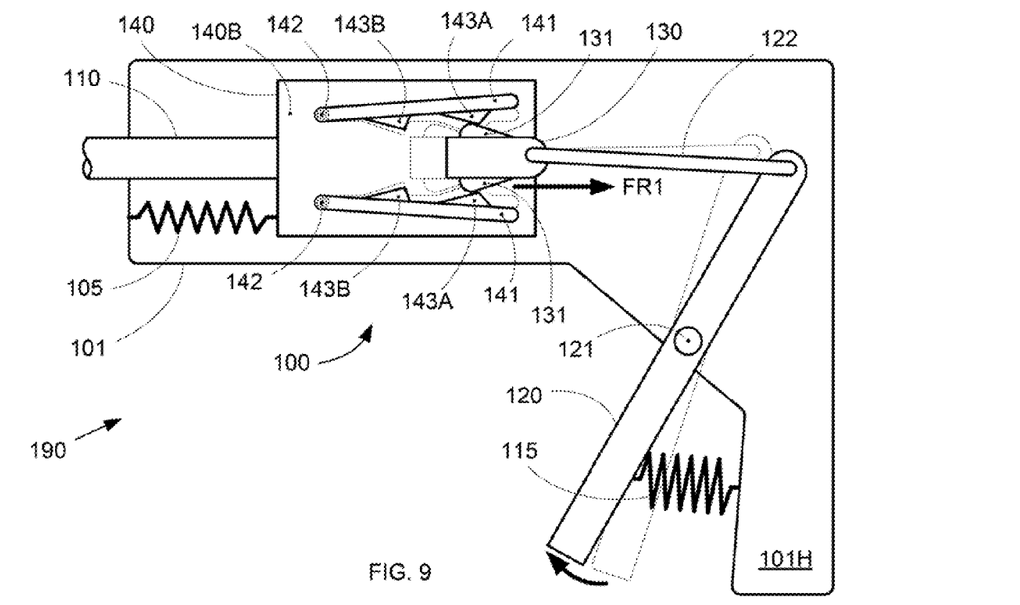
Figure 10:
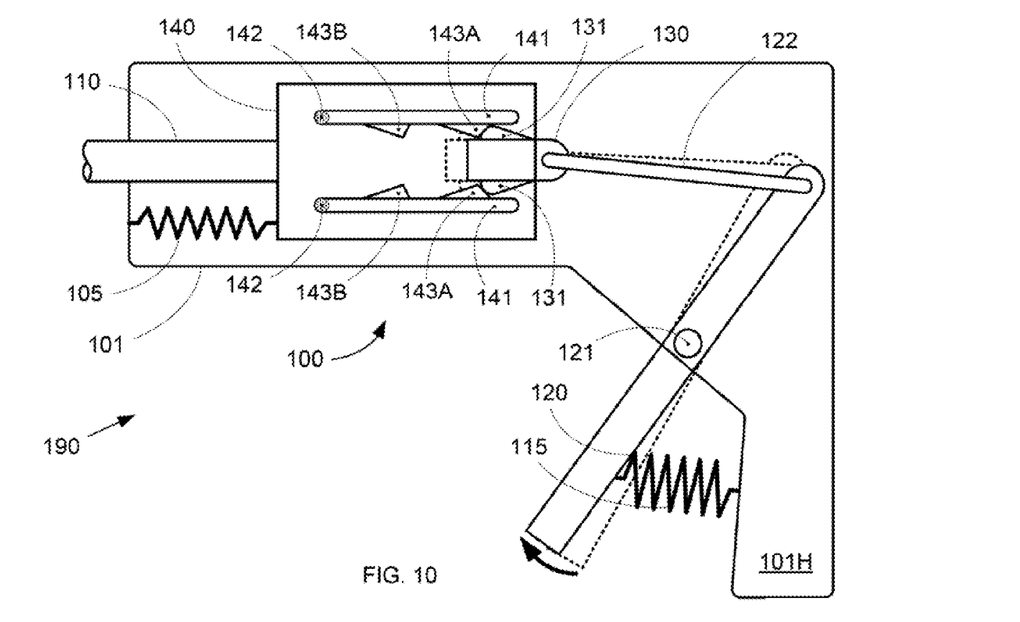

Continuing to pull actuator 120 away from handle 101H with a second reset force FR1 wedges drive features 131 between transmission features 143A, as shown in FIG. 9, and ultimately to the opposite side of transmission features 143A, thereby resetting the first break point of clutch 100 and placing it in its original condition, as shown in FIG. 10.

To enhance the usability of surgical instrument 190, it is desirable that the resetting operation require less force than the threshold forces required to trip the clutch breakpoints (i.e., reset forces FR1 and FR2 being less than threshold forces FT1 and FT2). Therefore, in various embodiments, drive features 131 and transmission features 143 can be configured to provide this "asymmetric" force requirement condition. For example, as shown in FIG. 11, the leading and trailing surfaces of transmission features 143 and drive features 131 can be tailored to more strongly resist motion of drive element 130 distally with respect to transmission element 140 (i.e., slip) than motion of drive element 130 proximally with respect to transmission element 140 (i.e., reset).

Figure 11:
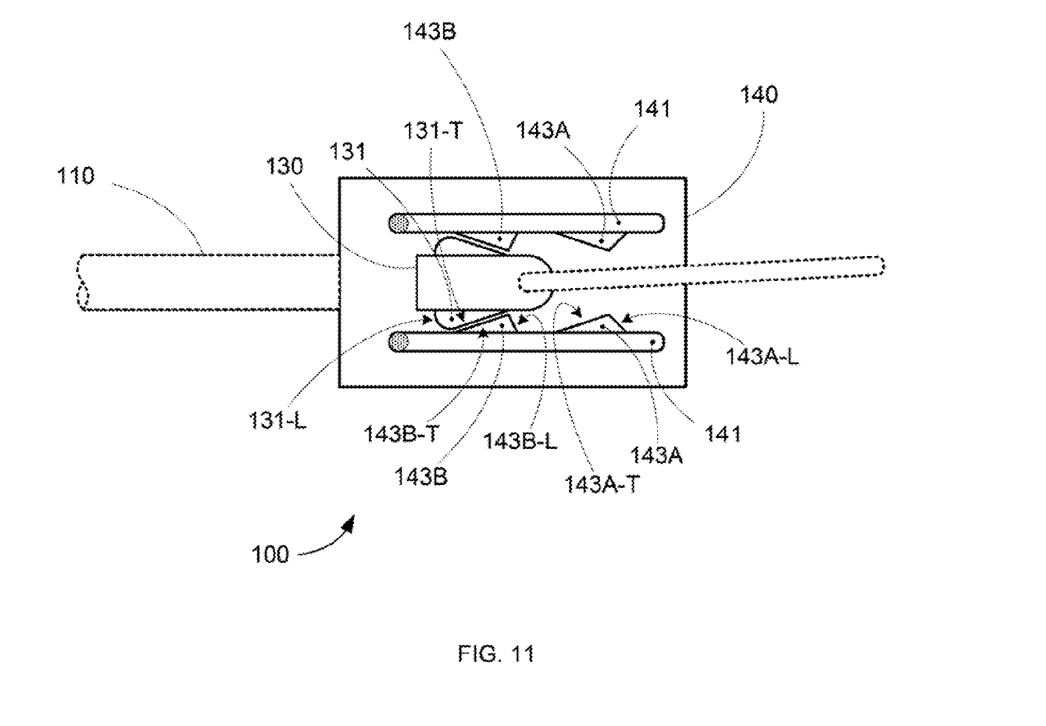
FIG. 11 is a detail view of the force-limiting clutch of FIGS. 1-2.

As shown in FIG. 11, in one embodiment, transmission features 143A and 143B can have leading surfaces 143A-L and 143B-L, respectively, that are angled much more steeply than the trailing surfaces 143A-T and 143B-T, respectively. Likewise, drive features 131 can have leading surfaces 131-L that are angled much more steeply than trailing surfaces 131-T. As a result, the force required to slide drive features 131 distally past transmission features 143 (i.e., the force required to trip the breakpoints of clutch 100) is much greater than the force required to slide drive features 131 proximally past transmission features 143 (i.e., the force required to reset clutch 100).

Note that although both drive features 131 and transmission features 143 are depicted as having more steeply inclined leading edges than trailing edges for exemplary purposes, in various other embodiments, any combination of surface inclinations can be incorporated into force-limiting clutch 100. For example, in one embodiment, only drive features 131 or only transmission features 143 could exhibit gentle trailing surface inclines, which would still reduce required reset forces compared to breakpoint trip forces.

Figure 12:
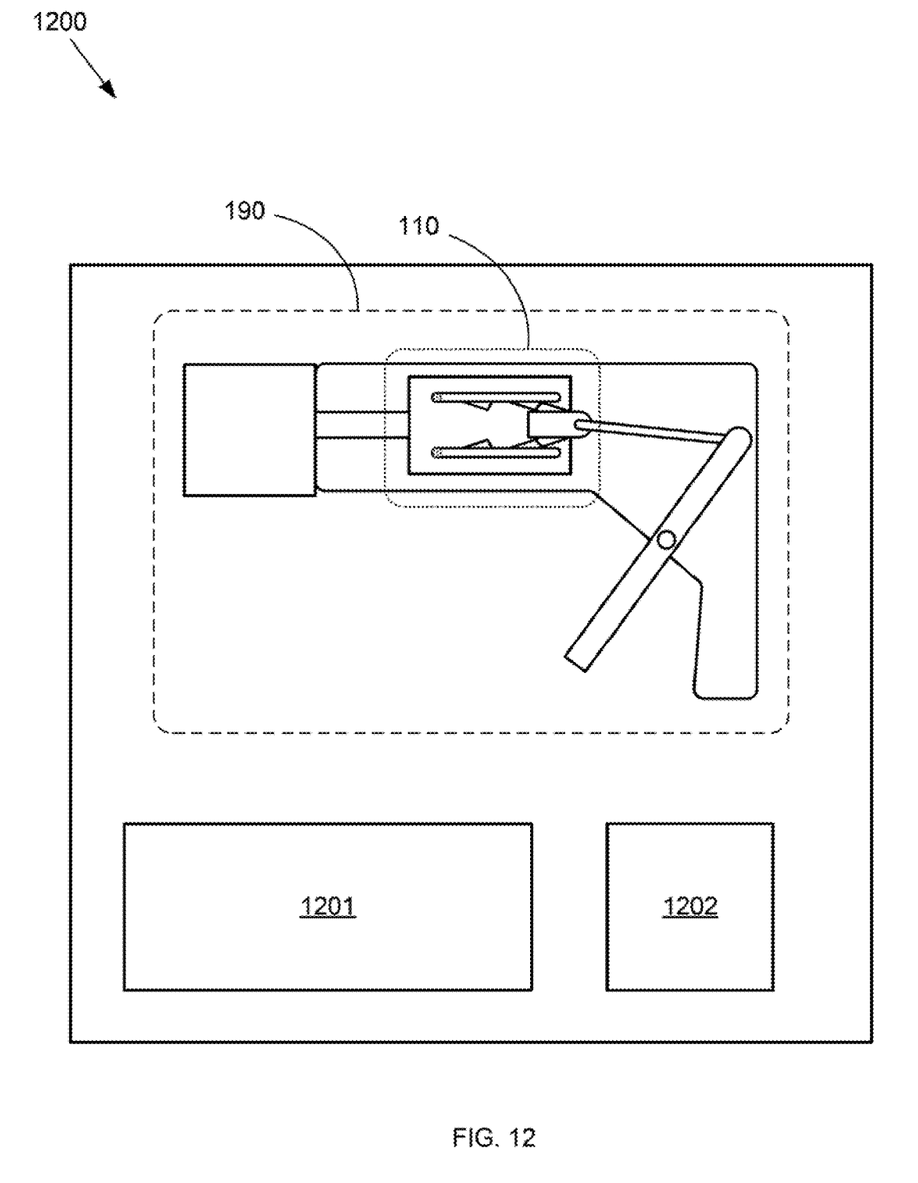
FIG. 12 is a block diagram of a surgical kit that includes the surgical instrument of FIGS. 1-2.

FIG. 12 shows a diagram of a kit 1200 for use in performing a surgical procedure. Kit 1200 includes a surgical instrument 190 (e.g., such as shown in FIG. 2A or 2B) that includes a force-limiting clutch 100 (as described with respect to FIGS. 1-11). Kit 1200 further includes optional additional instruments 1201 and optional directions for use 1202 that provide instructions for using surgical instrument 190 and optional additional instruments 1201 (e.g., instructions for performing a vertebroplasty or kyphoplasty procedure using surgical instrument 190 and optional additional instruments 1201).

For example, kit 1200 could be a kit for use in a kyphoplasty procedure, and surgical instrument 190 could be a system for delivering bone filler material (e.g., as described with respect to FIG. 2A), in which case optional additional instruments 1201 could be tools for creating a void in cancellous bone. Alternatively, kit 1200 could be a kit for use in a kyphoplasty procedure in which surgical instrument 190 is a cavity creation system (e.g., as described with respect to FIG. 2B), in which case optional additional instruments 1201 could be tools for delivering bone filler material to the void created by surgical instrument 190. Various other additional instruments 1201 will be readily apparent for various other surgical procedures.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A surgical system comprising:
a drive element defining a longitudinal axis and comprising a first set of drive features;
an actuator for applying a drive force to the drive element;
a transmission element comprising:
support elements; and
a first set of interfacing transmission features disposed on the support elements and being configured to form a passageway through which the drive element moves, wherein the support elements are cantilevered so as to flex apart and spring back as the drive element passes through the passageway; and
a drive shaft coupled to the transmission element,
wherein when the drive features are in direct contact with the support elements such that the drive element and the transmission element move together in parallel along the same axis in a first orientation when the drive force is less than a first threshold force, and the first set of drive features slips past the first set of transmission features in a first direction through the passageway when the drive force reaches the first threshold force.

2. The surgical system of claim 1, wherein the transmission element further comprises a second set of transmission features, and wherein when the first set of drive features are engaged with the second set of transmission features in a second orientation, the drive element and the transmission element move together when the drive force is less than a second threshold force, and the first set of drive features slip past the second set of transmission features in the first direction when the drive force reaches the second threshold force.

3. The surgical system of claim 2, wherein the first threshold force is substantially equal to the second threshold force.

4. The surgical system of claim 2, wherein the first threshold force is less than the second threshold force.

5. The surgical system of claim 1, wherein when the first set of drive features are engaged with the first set of transmission features in a second orientation, the first set of drive features slips past the first set of transmission features in a second direction when a reset force applied to the drive element reaches a second threshold force, wherein the second direction is opposite to the first direction, and wherein the second threshold force is less than the first threshold force.

6. The surgical system of claim 5, wherein the first set of drive features are located on a surface of the drive element, wherein each of the first set of drive features includes a leading surface and a trailing surface, wherein the leading surface of each of the first set of drive features abuts one of the first set of transmission features in the first orientation, wherein the trailing surface of each of the first set of drive features abuts one of the first set of transmission features in the second orientation, and wherein the leading surface is more steeply angled with respect to the surface of the drive element than the trailing surface for each of the first set of drive features.

7. The surgical system of claim 5, wherein the first set of transmission features is located on a surface of the transmission element, wherein each of the first set of transmission features includes a leading surface and a trailing surface, wherein the leading surface of each of the first set of transmission features abuts one of the first set of drive features in the first orientation, wherein the trailing surface of each of the first set of transmission features abuts one of the first set of drive features in the second orientation, and wherein the leading surface is more steeply angled with respect to the surface of the transmission element than the trailing surface for each of the first set of transmission features.

8. The surgical system of claim 7, wherein the first set of drive features is located on a surface of the drive element, wherein each of the first set of drive features includes a leading surface and a trailing surface, wherein the leading surface of each of the first set of drive features abuts the leading surface of one of the first set of transmission features in the first orientation, wherein the trailing surface of each of the first set of drive features abuts the trailing surface of one of the first set of transmission features in the second orientation, and wherein the leading surface is more steeply angled with respect to the surface of the drive element than the trailing surface for each of the first set of drive features.

9. The surgical system of claim 1, wherein the first set of drive elements is located on a surface of the drive element, wherein the transmission element further comprises a support structure, the first set of transmission elements being located on the support structure, wherein the support structure is configured to move away from the surface of the drive element and snap back on to the drive element as the first set of drive features slips past the first set of transmission features in the first direction to create an audible signal.

10. The surgical system of claim 9, wherein the transmission element further comprises a housing, the support structure being cantilevered off of the housing.

11. The surgical system of claim 1, further comprising a bone filler material delivery system for dispensing bone filler material in response to advancement of the drive shaft.

12. The surgical system of claim 1, further comprising an expandable element for creating a cavity within cancellous bone, the expandable element being expandable in response to advancement of the drive shaft.

13. A kit including a surgical instrument for performing a surgical procedure, the surgical instrument comprising:
 a drive element defining a longitudinal axis and comprising a first set of drive features;
 an actuator for applying a drive force to the drive element;
 a transmission element comprising:
  support elements; and
  a first set of interfacing transmission features disposed on the support elements and being configured to form a passageway through which the drive element moves, wherein the support elements are cantilevered so as to flex apart and spring back as the drive element passes through the passageway; and
 a drive shaft coupled to the transmission element,
 wherein when the drive features are in direct contact with the support elements such that the drive element and the transmission element move together in parallel along the same axis in a first orientation when the drive force is less than a first threshold force, and the first set of drive features slips past the first set of transmission features in a first direction when the drive force reaches the first threshold force.

14. The kit of claim 13, wherein the transmission element further comprises a second set of transmission features, and wherein when the first set of drive features are engaged with the second set of transmission features in a second orientation, the drive element and the transmission element move together when the drive force is less than a second threshold force, and the first set of drive features slip past the second set of transmission features in the first direction when the drive force reaches the second threshold force.

15. The kit of claim 13, wherein when the first set of drive features are engaged with the first set of transmission features in a second orientation, the first set of drive features slips past the first set of transmission features in a second direction when a reset force applied to the drive element reaches a second threshold force, wherein the second direction is opposite to the first direction, and wherein the second threshold force is less than the first threshold force.

16. The kit of claim 15, wherein the first set of drive features is located on a surface of the drive element, wherein each of the first set of drive features includes a leading surface and a trailing surface, wherein the leading surface of each of the first set of drive features abuts one of the first set of transmission features in the first orientation, wherein the trailing surface of each of the first set of drive features abuts one of the first set of transmission features in the second orientation, and wherein the leading surface is more steeply angled with respect to the surface of the drive element than the trailing surface for each of the first set of drive features.

17. The kit of claim 15, wherein the first set of transmission features is located on a surface of the transmission element, wherein each of the first set of transmission features includes a leading surface and a trailing surface, wherein the leading surface of each of the first set of transmission features abuts one of the first set of drive features in the first orientation, wherein the trailing surface of each of the first set of transmission features abuts one of the first set of drive features in the second orientation, and wherein the leading surface is more steeply angled with respect to the surface of the transmission element than the trailing surface for each of the first set of transmission features.

18. The kit of claim 13, wherein the first set of drive elements is located on a surface of the drive element, wherein the transmission element further comprises a support structure, the first set of transmission elements being located on the support structure, wherein the support structure is configured to move away from the surface of the drive element and snap back on to the drive element as the first set of drive features slips past the first set of transmission features in the first direction to create an audible signal.

19. The kit of claim 13, wherein the surgical instrument further comprises a bone filler material delivery system for dispensing bone filler material in response to advancement of the drive shaft, and wherein the kit further comprises directions for using the surgical instrument to deliver bone filler material to a vertebral body.

20. The kit of claim 13, wherein the surgical instrument further comprises an expandable element for creating a cavity within cancellous bone, the expandable element being expandable in response to advancement of the drive shaft, and wherein the kit further comprises a tool for delivering bone filler material to the cavity.

* * * * *